(12) United States Patent
Kim et al.

(10) Patent No.: US 9,713,500 B2
(45) Date of Patent: Jul. 25, 2017

(54) SURGICAL ROBOT CONTROL APPARATUS

(71) Applicant: SNU R&DB FOUNDATION, Seoul (KR)

(72) Inventors: Sungwan Kim, Seoul (KR); Youdan Kim, Seoul (KR); Hyeon Hoe Kim, Seoul (KR); Hee Chan Kim, Seoul (KR); Chan Gook Park, Seoul (KR); Choonghee Lee, Seoul (KR); Chiwon Lee, Paju-si (KR); Yong Hyun Park, Seoul (KR); Seungwoo Noh, Busan (KR); Chiyul Yoon, Seoul (KR)

(73) Assignee: SNU R&DB FOUNDATION, Seoul (KR)

( * ) Notice: Subject to any disclaimer, the term of this patent is extended or adjusted under 35 U.S.C. 154(b) by 318 days.

(21) Appl. No.: 14/714,800

(22) Filed: May 18, 2015

(65) Prior Publication Data

US 2015/0245876 A1 Sep. 3, 2015

Related U.S. Application Data

(63) Continuation-in-part of application No. 13/585,246, filed on Aug. 14, 2012, now abandoned.

(30) Foreign Application Priority Data

Oct. 25, 2011 (KR) .......................... 10-2011-0109426

(51) Int. Cl.
*A61B 1/00* (2006.01)
*A61B 19/00* (2006.01)
(Continued)

(52) U.S. Cl.
CPC .......... *A61B 19/2203* (2013.01); *A61B 34/30* (2016.02); *A61B 34/74* (2016.02);
(Continued)

(58) Field of Classification Search
CPC combination set(s) only.
See application file for complete search history.

(56) References Cited

U.S. PATENT DOCUMENTS 5,476,357 A 12/1995 Arai
5,882,206 A 3/1999 Gillio
(Continued)

FOREIGN PATENT DOCUMENTS

KR 10-2005-0100147 10/2005
KR 10-2007-0079052 8/2007
(Continued)

OTHER PUBLICATIONS

Allermann et al., "Joystick Interfaces are not Suitable for Robotized Endoscope Applied to Notes", Surgical Innovation, vol. 16, No. 2, Jun. 2009, pp. 111-116.

*Primary Examiner* — Thomas G Black
*Assistant Examiner* — Ana Thomas
(74) *Attorney, Agent, or Firm* — Hamre, Schumann, Mueller & Larson, P.C.

(57) ABSTRACT

Disclosed herein is a surgical robot control apparatus, in which a control stick member is connected to an upper surface of a base member, pivots and rotates around a connection portion, and is provided with a rotary button control member, a mode switching button member, and a control member which can be operated with the thumb. Thus, the surgical robot control apparatus can realize multiple functions. A surgeon can grasp the control stick member to easily control operation of a surgical robot and can perform other work using the other hand. Thereby, when performing surgery, the surgical robot control apparatus remarkably reduces the fatigue of the surgeon, thereby providing a surgical environment that is convenient and safe; and which provides maximized efficiency. Further, the surgical robot control apparatus can increase the safety of a patient using a safety device based on a buttons, software, and hardware while performing surgery.

20 Claims, 7 Drawing Sheets

(51) Int. Cl.
  *G05G 9/047* (2006.01)
  *B25J 13/02* (2006.01)
  *G06F 3/0338* (2013.01)
  *A61B 34/30* (2016.01)
  *A61B 34/00* (2016.01)

(52) U.S. Cl.
  CPC ............... *A61B 34/76* (2016.02); *B25J 13/02* (2013.01); *B25J 13/025* (2013.01); *G05G 9/047* (2013.01); *G05G 9/04788* (2013.01); *G06F 3/0338* (2013.01); *A61B 2034/742* (2016.02)

(56) References Cited

U.S. PATENT DOCUMENTS

| | | | | |
|---|---|---|---|---|
| 6,184,868 | B1* | 2/2001 | Shahoian | A63F 13/06 345/156 |
| 7,061,466 | B1* | 6/2006 | Moore | F16F 6/00 345/156 |
| 7,155,316 | B2 | 12/2006 | Sutherland et al. | |
| 2001/0026264 | A1* | 10/2001 | Rosenberg | A63F 13/06 345/156 |
| 2003/0030619 | A1* | 2/2003 | Martin | A63F 13/285 345/156 |
| 2003/0191455 | A1 | 10/2003 | Sanchez et al. | |
| 2010/0063630 | A1 | 3/2010 | Sutherland et al. | |
| 2011/0022229 | A1* | 1/2011 | Jang | B25J 3/04 700/248 |
| 2011/0234369 | A1 | 9/2011 | Cai et al. | |
| 2011/0277775 | A1* | 11/2011 | Holop | A61B 17/3423 128/849 |
| 2011/0301616 | A1 | 12/2011 | Sanchez et al. | |

FOREIGN PATENT DOCUMENTS

| | | |
|---|---|---|
| KR | 10-0925102 | 6/2009 |
| KR | 10-2010-0015516 | 12/2010 |

* cited by examiner

SURGICAL ROBOT CONTROL APPARATUS

CROSS REFERENCE TO RELATED APPLICATION(S)

This application is a continuation-in-part of U.S. Ser. No. 13/585,246, filed on Aug. 14, 2012, which claimed priority to Korean Patent Application No. 10-2011-0109426, filed on Oct. 25, 2011, all of which are hereby incorporated herein by reference in their entirety.

BACKGROUND OF THE INVENTION

1. Technical Field

The present invention relates generally to a surgical robot control apparatus and, more particularly, to a surgical robot control apparatus capable of controlling the operation of a surgical robot in a precise and easy manner with one hand when surgery is being performed, controlling the surgical robot that has various functions, greatly reducing the fatigue of a surgeon when performing surgery, and highly increasing the safety of a patient during the surgery because of the use of a safety device described below.

2. Description of the Related Art

In general, surgical robots refer to robots that are operated to perform surgery in place of a surgeon, and are controlled by a surgeon to perform the surgery.

The movements of such surgical robots are accurate and precise, and so there is a trend to increase their application. The surgical robots include an osteoplastic surgical robot, a laparoscopic surgical robot, a stereostatic surgical robot, and so on.

For example, the laparoscopic surgical robot is a robot that performs minimum invasive surgery using a laparoscope and small surgical instruments.

However, it is difficult to very precisely control such a surgical robot, and switches for controlling the robot is complicated, so that the surgeon should use both hands.

Further, the surgeon who performs surgery has no idea as to how much an end-effector has come into contact with a surgical spot, and thus it is difficult to perform surgery on a deep spot without damaging tissues.

SUMMARY OF THE INVENTION

Accordingly, the present invention has been made keeping in mind the above problems occurring in the related art, and an object of the present invention is to provide a surgical robot control apparatus capable of controlling operation of a surgical robot in a precise and easy manner when surgery is performed, greatly reducing the fatigue of a surgeon when the surgery is performed, and realizing multiple functions.

In order to accomplish the above object, the present invention provides a surgical robot control apparatus controlling an operation of a surgical robot having an end-effector. The surgical robot control apparatus includes: a base member; a control stick member having a lower end connected to the base member, the control stick member pivoting and rotating around a connection portion of the control stick member; a support member supporting the base member and including a first support portion connected to a lower end of the base member, a shaft portion connected to the first support portion, and a second support portion connected to an end of the shaft portion; a movable member on which the support member is mounted; and a control unit controlling the operation of the surgical robot based on manipulation of the control stick member and the support member.

The surgical robot control apparatus according to the present embodiment can accurately and precisely control the end-effector of the surgical robot during the surgery, thereby providing a more convenient and safe surgical environment when performing surgery, and remarkably reducing fatigue of the surgeon.

The surgical robot control apparatus can realize multiple functions, and perform a surgical function, which has been performed by both hands and/or the feet, using one hand, so that the other hand can perform other work. For this reason, the surgical robot control apparatus maximizes efficiency, so that it can reduce the fatigue caused by the use of inconvenient tools for a long time.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
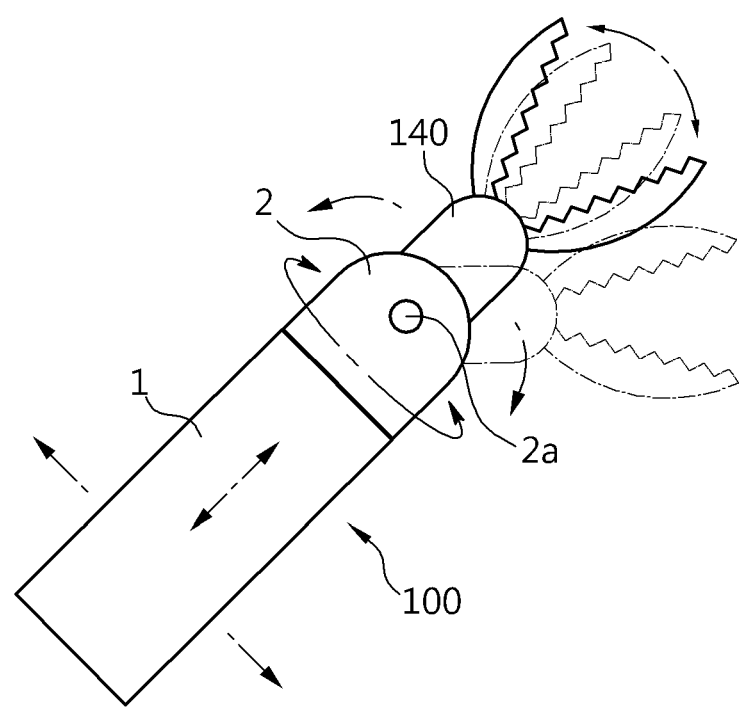
FIG. 1 shows an example of a surgical robot controlled by a surgical robot control apparatus according to an embodiment of the present invention.

Reference now should be made to an exemplary embodiment of the present invention with reference to the drawings, in which the same reference numerals are used throughout the different drawings to designate the same or similar components.

Referring to FIG. 1, a surgical robot 100 controlled by a surgical robot control apparatus according to an embodiment includes an arm body 1 that moves backwards/forwards in a lengthwise direction as well as left/right in a transverse direction perpendicular to the lengthwise direction.

A rotary body 2 is rotatably coupled to an end of the arm body 1. The rotary body 2 is rotatably coupled to the arm body 1 by a rotary shaft disposed in a lengthwise direction of the arm body 1. In the surgical robot control apparatus, an end-effector 140 is coupled to the rotary body 2 by a hinge and can pivot around the hinge.

The end-effector 140 is a device that performs surgery by making direct contact with the surgical spot. For example, in a flexible laparoscopic robot, a variety of instruments such as forceps, scissors, a camera system, a probe, and a needle may be used as the end-effector. In the present embodiment, forceps are used as an example.

The arm body 1 moves forwards, backwards, left, and right. The end-effector 140 pivots around the hinge of the rotary body 2, and rotates along with the rotary body 2, thereby coming into contact with the surgical spot.

Figure 2:
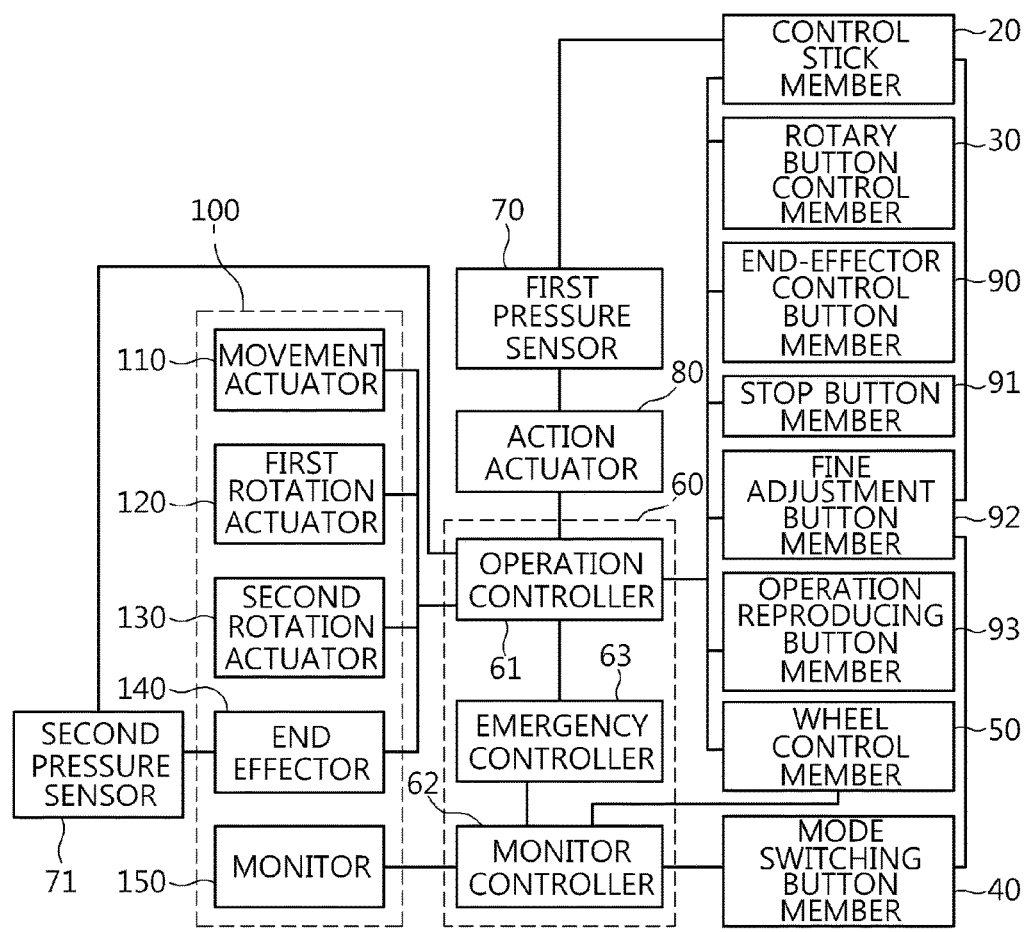
FIG. 2 is a block diagram showing the surgical robot control apparatus according to the embodiment.
Figure 3:
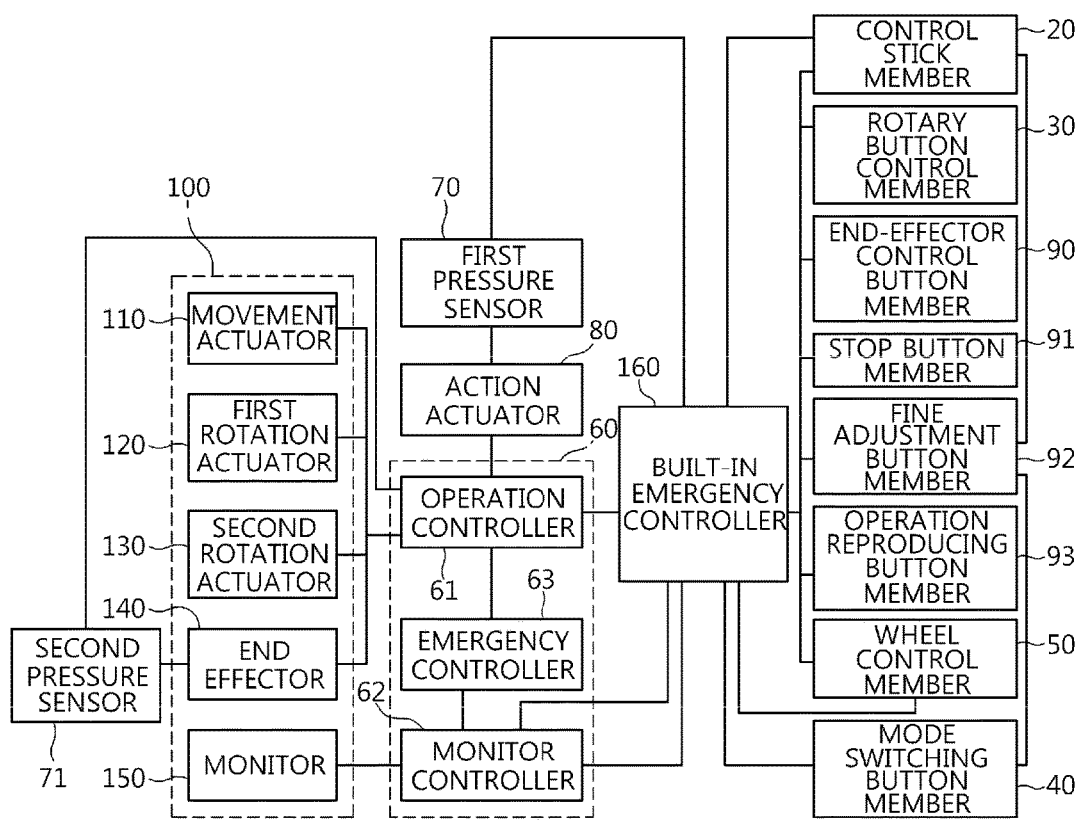
FIG. 3 is a block diagram showing a surgical robot control apparatus according to another embodiment.
Figure 4:
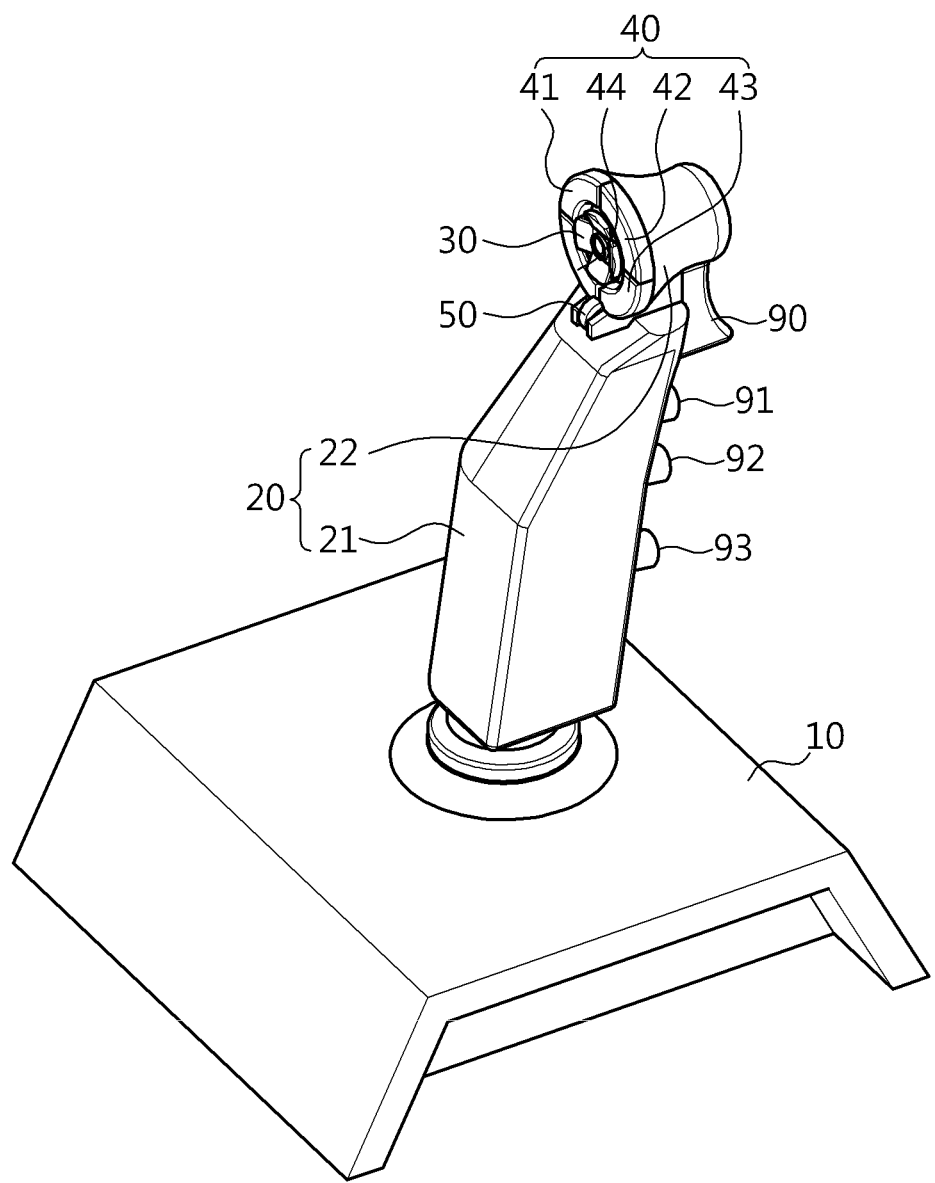
FIG. 4 is a perspective view showing the surgical robot control apparatus according to the embodiment.
Figure 5:
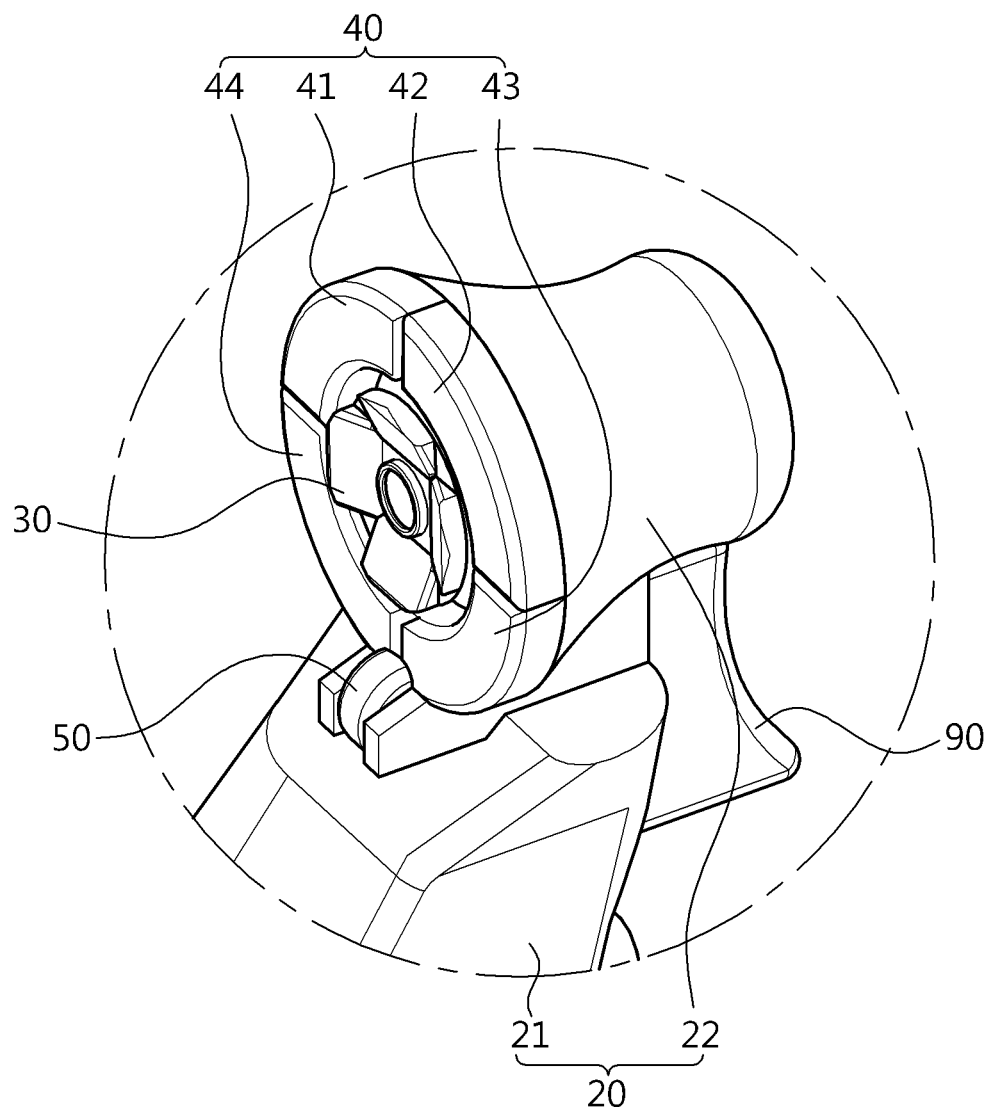
FIG. 5 is an enlarged perspective view showing main parts of the surgical robot control apparatus according to the embodiment.
Figure 6:
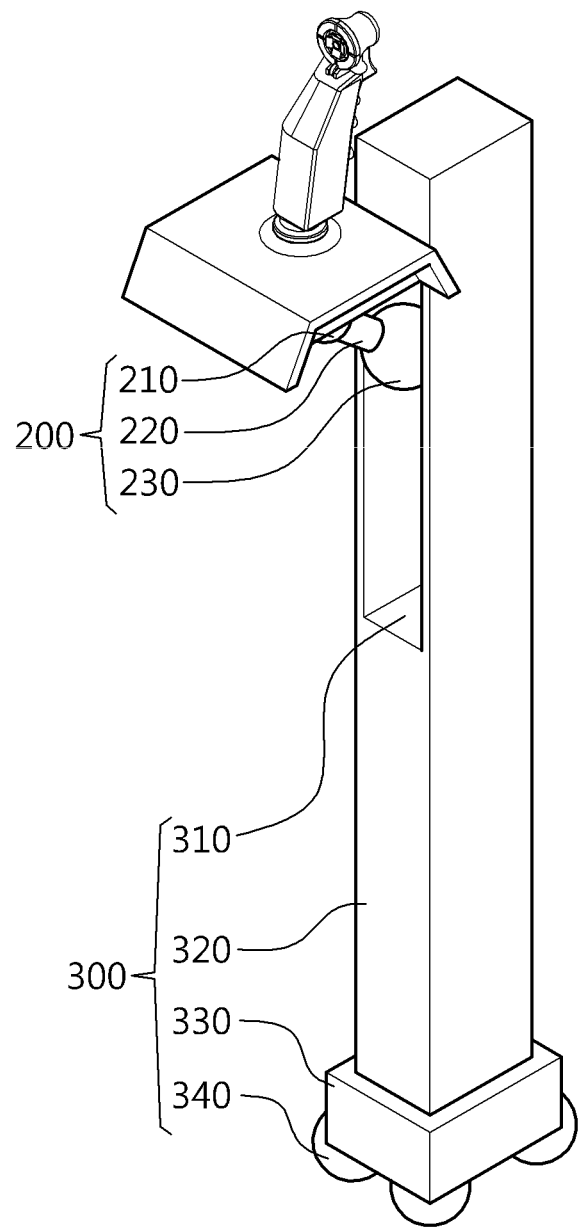
FIG. 6 is a perspective view showing a surgical robot control apparatus according to a further embodiment.
Figure 7:
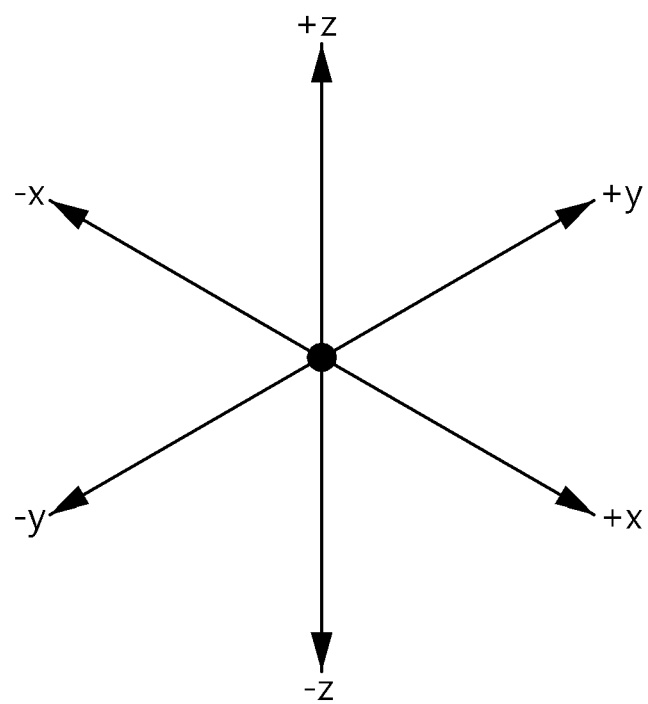
FIG. 7 shows lines representing a plurality of shafts, a reference of which is a first support portion.

Referring to FIG. 2, the surgical robot 100 further includes a movement actuator 110 forcing the arm body 1 to move forwards, backwards, leftwards, and rightwards, a first rotation actuator 120 rotating the rotary body 2, a second rotation actuator 130 pivoting the end-effector 140 around the hinge, and a monitor 150 photographing the surgical spot using a camera and displaying an image photographed by the camera on a screen.

Further, the surgical robot control apparatus according to the present embodiment includes a control unit 60 controlling the surgical robot 100. The control unit 60 includes an operation controller 61 that controls operations of the movement actuator 110, the first rotation actuator 120, the second rotation actuator 130, and the end-effector 140, and a monitor controller 62 that controls operation of the monitor 150.

The operation controller 61 is connected with a control stick member 20, a rotary button control member 30, a wheel control member 50, an end-effector control button member 90, a stop button member 91, a fine adjustment button member 92, an operation reproducing button member 93, and a mode switching button member 40, thereby controlling the operations of the movement actuator 110, the first rotation actuator 120, the second rotation actuator 130, and the end-effector 140. Further, the monitor controller 62 is connected with the mode switching button member 40, the wheel control member 50, and the fine adjustment button member 92, thereby controlling screen display of the monitor 150. The surgical robot control apparatus according to the present embodiment performs position adjustment and operation of the end-effector 140 by way of the control unit 60 in the surgical robot 100.

The surgical robot control apparatus according to the present embodiment will be described below in detail with reference to FIGS. 3 to 7.

The surgical robot control apparatus according to the present embodiment includes a base member 10.

A lower end of the control stick member 20 is connected to an upper surface of the base member 10. The lower end of the control stick member 20 and the base member 10 are connected by a ball joint. The control stick member 20 is connected so as to protrude from the upper surface of the base member 10, and pivots and rotates around a ball.

The base member 10 is connected to a support member 200. The support member 200 supports the total weight of the base member 10 and the control stick member 20. The support member 200 supports the base member 10 and includes a first support portion 210 connected to a lower end of the base member 10, a shaft portion 220 connected to the first support portion 210, and a second support portion 230 connected to an end of the shaft portion 220.

The first support portion 210 measures X-axis and Y-axis position information with respect to the first support portion 210 that serves as a reference point for the measurement of position. When the first support portion 210 performs motion in a direction, the end-effector 140 pivots on the fulcrum in a direction opposite to the direction in which the first support portion 210 moves, based on the X-axis and Y-axis position information of the first support portion 210. That is, the end-effector 140 performs fulcrum motion, responding to the motion of the first support portion 210.

The second support portion 230 measures Z-axis position information with respect to the first support portion 210 serving as a reference point. When the first support portion 210 performs motion, the end-effector 140 performs translational motion, based on the Z-axis position information of the first support portion 210.

This structure enables the control stick member 20 and the end-effector 140 to perform precise and accurate motion along with movement of the first support portion 210 and the second support portion 220. An end of the shaft portion 220 is connected to the first support portion 210 and the remaining end of the shaft portion 220 is connected to the second support portion 230.

The support member 200 is mounted on a movable member 300. The movable member 300 includes a recess 310 in which the second support portion 230 of the support member 200 can be inserted, a body 320 having the recess 310 therein, a movable base member 330 connected to a lower end of the body 320, and wheels 340 attached to a lower end of the movable base member 330.

The surgical robot control apparatus according to the present invention includes a controller 60 that controls the operation of the surgical robot control apparatus based on manipulation of the control stick member 20 and the support member 200.

The first support portion 210 is a ball joint and is connected to the lower end of the base member 10. The second support portion 230 is also a ball joint and is connected to the movable member 300. The first support portion 210 and the second support portion 220 can pivot and rotate around a ball.

A connection portion of the first support portion 210 which is connected to the base member 10 and a connection portion of the second support portion 230 which is connected to the movable member 300 are provided with respective sensors that measure position information. The sensors can measure +X-axis, −X-axis, +Y-axis, −Y-axis, +Z-axis, and −Z-axis position information with respect to the first support portion 210 serving as a reference point.

The first support portion 210 and the second support portion 230 may be provided with respective actuators for supporting a weight. The first support portion 210 supports the weight of the base member 10 so that the base member 10 can suitably maintain a horizontal body position. This enables a surgeon to easily manipulate the control stick member 20 at various angles.

The control stick member 20 is connected with the movement actuator 110 and the first rotation actuator 120 via the operation controller 61, and controls operations of the movement actuator 110 and the rotary body 2. The movement actuator 110 and the first rotation actuator 120 are connected with the control stick member 20 so as to have the same operating direction as the control stick member 20. That is, when the control stick member 20 moves forwards/backwards and thus transfers a forward/backward movement signal to the operation controller 61, the operation controller 61 receives the forward/backward movement signal, and operates the movement actuator 110 such that the arm body 1 moves forwards/backwards. When the control stick member 20 moves leftwards/rightwards and thus transfers a leftward/rightward movement signal to the operation controller 61, the operation controller 61 receives the leftward/rightward movement signal, and operates the movement actuator 110 so that the arm body 1 moves leftwards/rightwards. Further, when the control stick member 20 rotates about the ball and thus transfers a rotation signal based on a rotating direction to the operation controller 61, the operation controller 61 receives the rotation signal, and operates the first rotation actuator 120 such that the rotary body 2 rotates in the rotating direction of the rotation signal.

Meanwhile, the surgical robot control apparatus according to the present embodiment may further include a first pressure sensor 70 that is provided at a connection portion of the control stick member 20 and detects a manipulation force of the control stick member 20, a second pressure sensor 71 that is mounted on the end-effector 140 and detects a reaction force generated when the end-effector 140 comes into contact with the surgical spot, and an action actuator 80 that is provided at the connection portion of the control stick member 20 and acts on the pressure detected by the second pressure sensor 71.

The first pressure sensor 70, the second pressure sensor 71, and the action actuator are connected to the operation controller 61. The operation controller 61 rotates the rotary body 2 based on the manipulation force received from the first pressure sensor 70, and displays the intensity of the manipulation force on the screen of the monitor 150. Further, the operation controller 61 operates the action actuator 80 based on the reaction force received from the second pressure sensor 71, and transfers the reaction force to a surgeon who is performing surgery. The rotary button control member 30 rotating the rotary body 2 is mounted on the control stick member 20. The rotary button control member 30 is rotatably mounted on one surface of the control stick member 20, is connected to the operation controller 61, and transfers a rotation signal based on a rotating direction thereof to the operation controller 61. The operation controller 61 receives the rotation signal of the rotary button control member 30 and operates the second rotation actuator 130, thereby enabling the end-effector 140 to pivot around the hinge in a leftward/rightward direction.

The end-effector 140, which performs surgery by making contact with a surgical spot, is allowed to move forwards, backwards, leftwards, and rightwards by the movement actuator 110 and to rotate in directions perpendicular to each other by the first and second rotation actuators 120 and 130. Here, these actuators 110, 120 and 130 are operated by receiving the control signals of the control stick member 20 and the rotary button control member 30. The end-effector 140 can move at an angle that is greater than that of a human wrist, and thus realize movement that cannot be realized by a human hand. Further, the movement actuator 110, the first rotation actuator 120, and the second rotation actuator 130 are electrically powered, so that the end-effector 140 is more precisely driven to permit accurate surgery without creating vibrations.

The mode switching button member 40 of the control stick member 20 is provided with a plurality of buttons. The mode switching button member 40 switches a surgical mode of the surgical robot 100. At least one of the buttons of the mode switching button member 40 may be connected to the monitor controller 62 controlling the monitor 150 of the surgical robot 100, and control a mode of the monitor 150. The mode switching button member 40 includes a numerical value adjusting button 41 that is made up of two divided buttons and is allowed to adjust a numerical value displayed on the monitor 150 of the surgical robot 100 when surgery is performed, a camera mode button 42 that switches a camera mode of the surgical robot 100, a temporary stop button 43 that stops the movement of the end-effector 140, and a Bovie button 44 that conducts electricity to the end-effector 140 and is allowed to stop the bleeding at a surgical spot. The numerical value adjusting button 41 is configured so that two buttons are individually superimposed by way of example.

The Bovie button 44 gives an electrical stimulus only to a target organ or tissue by conducting electricity only to a part of the end-effector 140 which has come into substantial contact with the surgical spot, i.e. forceps, a needle, or scissors.

An example of the camera mode includes a zoom in/out mode, and a camera migration/stop mode. The mode switching button member 40 serves to enable a surgeon to change a travel speed of the end-effector 140 and the operation mode of the monitor 150 to rapidly set a surgical environment optimized to him/her, thereby providing a surgical environment in which functions that are impossible using an existing surgical interface can be easily set by one button. In the present embodiment, the button takes a pressurized button switch pressed to be operated by way of example.

The wheel control member 50 is mounted on the control stick member 20. The wheel control member 50 is rotatably coupled to a wheel fixture protruding from one surface of the control stick member 20, and adjusts the manipulation force of the end-effector 140. The wheel control member 50 is connected to the end-effector 140, is based on fine adjustment of the operation of the end-effector 140, and is used to perform precise surgery using the end-effector 140 in the state in which the end-effector 140 is stopped. For example, the wheel control member 50 adjusts the manipulation force of the end-effector 140 when the end-effector 140 precisely cuts out a part of tissue at the surgical spot or clamps the tissue. The wheel control member 50 may be connected to the mode switching button member 40, and particularly be used to control the operation of the mode switching button member 40. For example, the wheel control member 50 is connected with the numerical value adjusting button 41, the camera mode button 42, the temporary stop button 43, and the Bovie button 44, and is used to precisely adjust a magnitude of an input when the input is required to be adjusted to a very precise range. The wheel control member 50 may be used to increase or decrease the size of the surgical screen of the monitor 150 in camera mode, and to temporarily stop each operation.

Further, the control stick member 20 includes a stick body 21 grasped with the hand, and a thumb cradle body 22 that is located at an upper portion of the stick body 21 and allows a thumb of the hand grasping the stick body 21 to be located in front thereof. The rotary button control member 30, the buttons of the mode switching button member 40, and the wheel control member 50 may be provided on a front surface of the thumb cradle body 22.

The rotary button control member 30 is disposed at a central portion in the front surface of the thumb cradle body 22. The buttons of the mode switching button member 40 are disposed around the rotary button control member 30 at a distance. The wheel control member 50 is disposed at a lower portion of the thumb cradle body 22. The rotary button control member 30, the buttons of the mode switching button member 40, and the wheel control member 50 can be controlled by the thumb of a surgeon who is performing surgery in the state in which the surgeon is grasping the stick body 21, and thus may provide a convenient and safe surgical environment for the surgeon.

Meanwhile, the surgical robot control apparatus according to the present embodiment may further include the end-effector control button member 90 that is installed on the control stick member 20 and controls the operation of the end-effector 140. The end-effector control button member 90 is a pressurized button switch pressed to be operated, is connected with the end-effector 140 via the operation controller 61, and controls the operation of the end-effector 140.

As an example, when a surgeon presses the end-effector control button member 90, the forceps are closed. When the end-effector control button member 90 is released, the forceps are opened. As another example, providing that the end-effector 140 is scissors, when the end-effector control button member 90 is pressed, the scissors cut a surgical spot of interest.

The operation of the end-effector 140 caused by the operation of the end-effector control button member 90 is dependent on a type of the end-effector 140. The end-effector control button member 90 may be provided to the control stick member 20 so as to be operated by any one of the index finger, middle finger, ring finger, and little finger of the hand grasping the control stick member 20. Since the end-effector control button member 90 can be operated by any one of the index finger, middle finger, ring finger, and little finger of the hand grasping the control stick member 20, the end-effector control button member 90 can be easily operated while the control stick member 20 is operated.

Preferably, a sensor that measures the pressure being exerted on the end-effector control button member 90 is installed inside the end-effector control button member 90 in order to adjust the manipulation force of the end-effector 140. The sensor may be a pressure sensor, a force sensor, or a combination of both types of sensors.

For example, when the pressing force exerted on the end-effector control button member 90 is increased, the gripping force of the forceps is also increased. Conversely, when the pressing force exerted on the end-effector control button member 90 is decreased, the gripping force of the forceps is also correspondingly decreased. That is, it is possible to adjust the manipulation force of the end-effector 140 such as forceps, using the pressing force exerted on the end-effector control button member 90, thereby enabling very delicate surgery.

The surgical robot control apparatus according to the present embodiment may further include the stop button member 91 that is installed on the control stick member 20 and stops overall operation of the surgical robot 100. The stop button member 91 is a pressurized button that is pressed to be operated, is connected to the surgical robot 100 via the operation controller 61, and immediately stops overall operation of the surgical robot 100 in an emergency to secure safety of the patient and to cope with the state of emergency while performing the surgery. The stop button member 91 may be provided to the control stick member 20 so as to be operated by any one of the index finger, middle finger, ring finger, or little finger of the hand grasping the control stick member 20. Since the stop button member 91 can be operated by any one of the index finger, middle finger, ring finger, or little finger of the hand of a surgeon who is grasping the control stick member 20, the stop button member 91 can be easily operated while the control stick member 20 is being manipulated. The stop button member 91 is operated by the hand of the surgeon when the surgeon senses danger. Since the surgeon performs surgery with the aid of the monitor 150, the surgeon may fail to recognize that the end-effector 140 moves to a movement restricted region. Thus, a range within which the end-effector 140 should not come into contact is set to an image displayed on the monitor 150, and when the end-effector 140 moves to the set range while performing surgery, a function of automatically detecting this situation to interrupt any operation inputs from the components installed on the control stick member may be provided. In the present embodiment, the control unit may further include an emergency controller 63 that is connected to the operation controller 61 and the monitor controller 62 controlling the operation of the monitor 150, and stops operation when the end-effector 140 is located in its movement restricted range set to the image displayed on the monitor 150. The emergency controller 62 stops movement and operation of the end-effector 140 when the end-effector 140 is located within the movement restricted range set to the image of the surgical spot displayed on the monitor 150, thereby making it possible to perform surgery more safely.

The surgical robot control apparatus according to the present embodiment may further include a built-in emergency controller 160. The built-in emergency controller 160 has its own control processing unit (CPU) in an operation device. The built-in emergency controller 160 checks chips installed in all the operation devices and button members of the surgical robot control apparatus for abnormal operations in terms of hardware. It also continuously monitors a main controller to check for abnormal operations.

The emergency controller 63 resides in a main controller such as a computer and performs monitoring to check the chips in the apparatus for abnormal operations in terms of software. The built-in emergency controller 160 performs monitoring to check the chips in the operation devices and button members for abnormal operations in terms of hardware by interlocking with the emergency controller 63. That is, double monitoring can be performed.

The control stick member 20 of the surgical robot control apparatus according to the present embodiment is not a joystick for general use but a manipulation member for medical care. Therefore, it is necessary to continuously ensure the safety of the control stick member 20. Furthermore, it is preferable that the surgical robot control apparatus be equipped with a double emergency controller including the emergency controller 63 for monitoring execution of software algorithm and the built-in emergency controller 160 for monitoring operation of hardware.

The surgical robot control apparatus according to the present embodiment may further include the fine adjustment button member 92 that is installed on the control stick member 20 and expands the resolution while reducing the range of input values when operated. The fine adjustment button member 92 is connected to the control stick member 20 or the mode switching button member 40, and is allowed to precisely control the operation of the control stick member 20 or the mode switching button member. The fine adjustment button member 92 allows fine control by expanding the resolution while reducing the input value range. That is, when a surgeon requires very fine adjustment of the movement of the end-effector 140 when performing surgery, the surgeon operates the control stick member 20 while pressing the fine adjustment button member 92. Thereby, the motion of the end-effector 140 can be controlled very precisely.

Further, when the image displayed on the monitor 150 is zoomed in or out, or when the magnitude of the input value input to the monitor 150 is reduced or increased, very precise control is possible by operating the control stick member 20 while pressing the fine adjustment button member 92. The fine adjustment button member 92 may be provided to the control stick member 20 so as to be operated by any one of the index finger, middle finger, ring finger, or little finger of the hand grasping the control stick member 20. Since the fine adjustment button member 92 can be operated by any one of an index finger, a middle finger, a ring finger, and a little finger of the hand grasping the control stick member 20, the fine adjustment button member 92 can be easily operated while the control stick member 20 is being manipulated.

The surgical robot control apparatus according to the present embodiment may further include the operation reproducing button member 93 that is installed on the control stick member 20 and reproduces a stored operation. Preset operations of the end-effector 140 are stored in the operation controller 61, and the operation reproducing button member 93 is allowed to repeat the preset operations stored in the operation controller 61. The preset operations of the end-effector 140 include a precise complicated operation such as suturing, and are dependent on the type of the end-effector 140. Depending on the type of the end-effector 140, a variety of stored operations are selected and performed. That is, when a precise, complicated operation such as suturing is repetitively performed when performing surgery, convenience is improved. The operation reproducing button member 93 may be provided to the control stick member 20 so as to be operated by any one of the index finger, middle finger, ring finger, and little finger of the hand grasping the control stick member 20. Since the operation reproducing button member 93 can be operated by any one of the index finger, middle finger, ring finger, and little finger of the hand grasping the control stick member 20, the operation reproducing button member 93 can be easily operated while the control stick member 20 is being manipulated.

The surgical robot control apparatus according to the present embodiment may further include at least any one member selected from among the end-effector control button member 90, the stop button member 91, the fine adjustment button member 92, and the operation reproducing button member 93 which are all installed on the control stick member 20.

Meanwhile, the end-effector control button member 90, the stop button member 91, the fine adjustment button member 92, and the operation reproducing button member 93 may be disposed on the control stick member 20 so as to be operated by different fingers including the index finger, middle finger, ring finger, and little finger of the hand grasping the control stick member 20. In the present embodiment, as an example, the end-effector control button member 90, the stop button member 91, the fine adjustment button member 92, and the operation reproducing button member 93 are sequentially disposed spaced apart from a rear upper portion of the stick body 21 so as to be able to be operated by the index finger, the middle finger, the ring finger, and the little finger respectively.

The surgical robot control apparatus according to the present embodiment is configured so that, while the surgeon grasps and operates the control stick member 20 with one hand, the rotary button control member 30, the buttons of the mode switching button member 40, and the wheel control member 50 can be operated by the thumb, and the end-effector control button member 90, the stop button member 91, the fine adjustment button member 92, and the operation reproducing button member 93 can be operated by the index finger, the middle finger, the ring finger, and the little finger.

The mode switching button member 40, the end-effector control button member 90, the stop button member 91, the fine adjustment button member 92, and the operation reproducing button member 93 may be freely modified depending on the type of end-effector 140, the surgical technique, the convenience of control for a surgeon, or the like. Further, it should be noted that other buttons may be added to suit the type of the end-effector 140, the surgical technique, the control convenience of a surgeon, or the like, and that the mode switching button member 40, the end-effector control button member 90, the stop button member 91, the fine adjustment button member 92, and the operation reproducing button member 93 may change the setting of the end-effector 140.

At least one button member among the button members may be equipped with a haptic portion that provides haptic feedback according to the pressure detected by the second pressure sensor 71.

The haptic portion is a module that provides tactile haptic feedback, and thus it enables a surgeon to feel tactile sensation based on the pressure detected by the second pressure sensor 71.

Actuating cells that give tactile sensation may be made of known devices such as balloon actuators or micro actuators that transfer linear motion to fingers or palm.

One example of the surgical robot controlled by the surgical robot control apparatus according to the present embodiment is a surgical robot that has only one invasive spot for the surgical spot, such as a single port surgical robot that performs surgery after several tracars are inserted through a single port. The single port surgical robot performs surgery using a hole made only in one place in the body of a patient to reach a target organ. Further, another example of the surgical robot controlled by the surgical robot control apparatus according to the present embodiment is a multi-port surgical robot. The multi-port surgical robot performs surgery using several holes made in the body of a patient to reach a target organ and tracars inserted through the respective holes. Yet another example of the surgical robot controlled by the surgical robot control apparatus according to the present embodiment is a natural orifice translumenal endoscopic surgery (NOTES) surgical robot. The NOTES surgical robot inserts a surgical instrument through the opening of a human body such as the mouth, anus, or vagina, and penetrates an inner wall of an organ to perform surgery. These surgical robots are merely examples of the surgical robot controlled by the surgical robot control apparatus according to the present embodiment. The surgical robot control apparatus according to the present embodiment is connected with any surgical robot to which the surgical robot control apparatus can be applied regardless of the surgical robot and the surgical method, and is used to be able to easily and accurately perform surgery using a variety of surgical methods.

The surgical robot control apparatus according to the present embodiment is able to control the end-effector 140 of the surgical robot 100 so as to be able to provide accurate and precise surgery, to remarkably reduce the fatigue of the surgeon, and to realize multiple functions, thereby providing a more convenient and safe surgical environment. Further, the surgical robot control apparatus is allowed to perform a surgical function, which has been performed by both hands and/or the feet, using one hand, so that other work using the other hand is possible. For this reason, the surgical robot control apparatus maximizes efficiency, so that it can reduce the fatigue caused by the use of inconvenient tools for a long time.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A surgical robot control apparatus controlling an operation of a surgical robot having an end-effector, comprising:
   a base member;
   a control stick member having a lower end connected to the base member, the control stick member pivoting and rotating around a connection portion of the control stick member;
   a support member supporting the base member and including a first support portion connected to a lower end of the base member, a shaft portion connected to the first support portion, and a second support portion connected to an end of the shaft portion;

a movable member on which the support member is mounted; and a control unit controlling the operation of the surgical robot based on manipulation of the control stick member.

2. The surgical robot control apparatus as set forth in claim 1, wherein the control unit moves an arm body of the surgical robot in forward, backward, leftward, and rightward directions and rotates a rotary body rotatably coupled to an end of the arm body based on the manipulation of the control stick member.

3. The surgical robot control apparatus as set forth in claim 2, further comprising:
   a rotary button control member that is rotatably mounted on one surface of the control stick member and pivots the end-effector hinged to the rotary body around a hinge;
   a mode switching button member that is installed on the control stick member and switches a surgical mode of the surgical robot; and
   a wheel control member that is rotatably mounted on the control stick member and adjusts a manipulation force of the end-effector.

4. The surgical robot control apparatus as set forth in claim 3, wherein the mode switching button member includes a plurality of buttons, at least one of which is connected to a monitor controller controlling a monitor of the surgical robot and controls a mode of the monitor.

5. The surgical robot control apparatus as set forth in claim 3, wherein:
   the control stick member includes a stick body grasped by one hand, and a thumb cradle body disposed at an upper portion of the stick body and allowing a thumb of the hand grasping the stick body to be located in front thereof; and
   the rotary button control member, the mode switching button member, and the wheel control member are installed on a front surface of the thumb cradle body.

6. The surgical robot control apparatus as set forth in claim 5, further comprising an end-effector control button member that is installed on the control stick member and controls an operation of the end-effector.

7. The surgical robot control apparatus as set forth in claim 6, further comprising: at least one of the following:
   a stop button member that is installed on the control stick member and stops overall operation of the surgical robot;
   a fine adjustment button member that is installed on the control stick member and expands a resolution while reducing a range of a value input when operated; and
   an operation reproducing button member that is installed on the control stick member and reproduces preset operations of the end-effector which are stored in the control unit.

8. The surgical robot control apparatus as set forth in claim 7, wherein the end-effector control button member, the stop button member, the fine adjustment button member, and the operation reproducing button member are disposed on the control stick member so as to be operated by different fingers including an index finger, a middle finger, a ring finger, and a little finger of the hand grasping the control stick member.

9. The surgical robot control apparatus as set forth in claim 7, wherein the end-effector control button member, the stop button member, the fine adjustment button member, and the operation reproducing button member are disposed on an upper portion of a rear surface of the stick body of the control stick member and arranged to be distanced from each other so as to be operated by an index finger, a middle finger, a ring finger, and a little finger of the hand grasping the control stick member, respectively.

10. The surgical robot control apparatus as set forth in claim 7, wherein at least one of the button members is provided with a haptic portion that provides haptic feedback according to a pressure detected by the second pressure sensor.

11. The surgical robot control apparatus as set forth in claim 6, further comprising a sensor that is installed in the end-effector control button member and measures a pressure exerted on the end-effector control button member to adjust manipulation force of the end-effector.

12. The surgical robot control apparatus as set forth in claim 1, wherein the first support portion measures X-axis and Y-axis position information with respect to the first support portion, serving as a reference point.

13. The surgical robot control apparatus as set forth in claim 12, wherein the end-effector moves forwards, backwards, left, and right; and pivots in directions perpendicular to each other by operations of a movement actuator, a first rotation actuator, and a second rotation actuator.

14. The surgical robot control apparatus as set forth in claim 12, wherein the end-effector operates in a direction in which the end-effector pivots on fulcrum when the first support portion performs motion in an X-axis direction and a Y-axis direction.

15. The surgical robot control apparatus as set forth in claim 12, wherein the second support portion measures Z-axis position information with respect to the first support portion serving as a reference point.

16. The surgical robot control apparatus as set forth in claim 15, wherein a connection portion of the first support portion and a connection portion of the second support portion are provided with respective sensors that measure position information.

17. The surgical robot control apparatus as set forth in claim 15, wherein a connection portion of the first support portion and a connection portion of the second support portion are provided with respective actuators that support the support member.

18. The surgical robot control apparatus as set forth in claim 1, wherein the control unit includes:
   an operation controller that controls movement and operation of the end-effector based on the operation of the control stick member;
   a monitor controller that controls operation of the monitor displaying a surgical spot image on a screen; and
   an emergency controller that is connected to the operation controller and the monitor controller, sets a movement restricted range of the end-effector to the image displayed on the monitor, and stops operation thereof when the end-effector is located in the movement restricted range.

19. The surgical robot control apparatus as set forth in claim 18, further comprising a built-in emergency controller that is built in the surgical robot control apparatus and monitors chips installed in the apparatus in terms of hardware by interlocking with the emergency controller for the purpose of double monitoring.

20. The surgical robot control apparatus as set forth in claim 1, further comprising:

a first pressure sensor that is provided at the connection portion of the control stick member and detects a manipulation force of the control stick member;

a second pressure sensor that is mounted on the end-effector and detects a reaction force generated when the end-effector comes into contact with a surgical spot; and an action actuator that is provided at the connection portion of the control stick member and acts on a pressure detected by the second pressure sensor.

* * * * *